(12) United States Patent
Kuroda et al.

(10) Patent No.: US 9,169,520 B2
(45) Date of Patent: Oct. 27, 2015

(54) CANCER MARKER, METHOD FOR EVALUATION OF CANCER BY USING THE CANCER MARKER, AND EVALUATION REAGENT

(71) Applicants: Masahiko Kuroda, Tokyo (JP); Masami Tanaka, Fukuoka (JP); Kosuke Oikawa, Kunitachi (JP); Takayuki Mizutani, Tokyo (JP); Masakatsu Takanashi, Isehara (JP); Seiko Iizuka, Tokyo (JP); Yoshinori Kosugi, Tokyo (JP); Kazuma Ohyashiki, Tokyo (JP); Akihiko Tsuchida, Tokyo (JP)

(72) Inventors: Masahiko Kuroda, Tokyo (JP); Masami Tanaka, Fukuoka (JP); Kosuke Oikawa, Kunitachi (JP); Takayuki Mizutani, Tokyo (JP); Masakatsu Takanashi, Isehara (JP); Seiko Iizuka, Tokyo (JP); Yoshinori Kosugi, Tokyo (JP); Kazuma Ohyashiki, Tokyo (JP); Akihiko Tsuchida, Tokyo (JP)

(73) Assignees: NEC CORPORATION, Tokyo (JP); TOKYO MEDICAL UNIVERSITY, Tokyo (JP)

( * ) Notice: Subject to any disclaimer, the term of this patent is extended or adjusted under 35 U.S.C. 154(b) by 0 days.

(21) Appl. No.: 14/039,835

(22) Filed: Sep. 27, 2013

(65) Prior Publication Data
US 2014/0170648 A1     Jun. 19, 2014

Related U.S. Application Data

(62) Division of application No. 13/472,190, filed on May 15, 2012, now Pat. No. 8,632,967, which is a division of application No. 12/990,330, filed as application No. PCT/JP2009/058421 on Apr. 28, 2009, now abandoned.

(30) Foreign Application Priority Data

Apr. 30, 2008   (JP) ................................. 2008-119280

(51) Int. Cl.
    *C12Q 1/68* (2006.01)
(52) U.S. Cl.
    CPC ........ *C12Q 1/6886* (2013.01); *C12Q 2600/158* (2013.01); *C12Q 2600/178* (2013.01)
(58) Field of Classification Search
    None
    See application file for complete search history.

(56) References Cited

U.S. PATENT DOCUMENTS

| 2007/0161004 A1* | 7/2007 | Brown et al. ........... 435/6 |
| 2009/0075258 A1 | 3/2009 | Latham et al. |
| 2009/0092974 A1* | 4/2009 | Davison et al. ........ 435/6 |
| 2009/0233297 A1* | 9/2009 | Mambo et al. ......... 435/6 |

FOREIGN PATENT DOCUMENTS

| WO | 2005/118806 A2 | 12/2005 |
| WO | 2007/081680 A2 | 7/2007 |
| WO | 2007-112754 A2 | 10/2007 |
| WO | 2008/036765 A2 | 3/2008 |
| WO | 2008/045505 A2 | 4/2008 |
| WO | 2008/061537 A2 | 5/2008 |
| WO | 2008/073915 A2 | 6/2008 |
| WO | 2008/136971 A1 | 11/2008 |
| WO | 2009/045356 A2 | 4/2009 |
| WO | 2009/059016 A1 | 5/2009 |
| WO | 2009/111643 A2 | 9/2009 |

OTHER PUBLICATIONS

Lui, et al., "Patterns of Known and Novel Small RNAs in Human Cervical Cancer," Cancer Res 2007, Jul. 1, 2007, pp. 6031-6043, vol. 67, No. 13.
Calin et al., "MicroRNA profiling reveals distinct signatures in B cell chronic lymphocytic leukemias," PNAS, 2004, vol. 101, No. 32, pp. 11755-11760.
He et al., "A microRNA polycistron as a potential human oncogene", Nature, 2005, vol. 435, pp. 828-833.
Chim et al,. "Detection and Characterization of Placental MicroRNAs in Maternal Plasma", Clinical Chemistry, 2008, vol. 54, No. 3, pp. 482-490.
O'Donnell et al., "c-Myc-regulated microRNAs modulate E2F1 expression", Nature, 2005, vol. 435, pp. 839-843.
Griffiths-Jones et al., "miRBase: tools for microRNA genomics", Nucleic Acids Research, 2008, vol. 36, D154-D158.
Ota et al., "Identification and Characterization of a Novel Gene, C13orf25, as a Target for 13q31-q32 Amplification in Malignant Lymphoma" Cancer Research, 2004, vol. 64, pp. 3087-3095.
Mizutani, et al., Its a small miRNA World, Biophysical Chemistry, 2007, pp. 211-214, vol. 51, No. 3.
Kuroda et al., "MicroRNAs as Biomarkers in Human Cancer" Experimental Medicine, 2009, vol. 27, No. 8, pp. 1223-1227 with partial translation.
Mitchell et al., "Circulating microRNAs as stable blood-based markers for cancer detection", PNAS, 2008, vol. 105, No. 30, pp. 10513-10518.

(Continued)

*Primary Examiner* — Kimberly Chong
(74) *Attorney, Agent, or Firm* — Sughrue Mion, PLLC

(57) ABSTRACT

The present invention provides a novel cancer marker for evaluating the onset, the preclinical stage, the clinical stage, or the prognosis of a cancer in a subject, and an evaluation method using the same. A cancer marker containing at least one miRNA selected from hsa-miR-92 and hsa-miR-494 is used as a marker for cancers excluding breast cancer. A method for evaluating the possibility of cancers excluding breast cancer includes the step of detecting the expression level of a cancer marker in a biological sample collected from a subject. In this method, the cancer marker contains at least one miRNA selected from hsa-miR-92 and hsa-miR-494.

22 Claims, 2 Drawing Sheets
(1 of 2 Drawing Sheet(s) Filed in Color)

(56) References Cited

OTHER PUBLICATIONS

Uziel et al., "The miR-17~92 cluster collaborates with the Sonic Hedgehog pathway in medulloblastoma", PNAS, 2009, vol. 106, No. 8, pp. 2812-2817.
Gilad et al., "Serum MicroRNAs Are Promising Novel Biomarkers", PLoS ONE, 2008, vol. 3, Iss.9, e3148.
Chen et al., "Complementary analysis of microRNA and mRNA expression during phorbol 12-myristate 13-acetate(TPA)-induced differentiation of HL-60 cells", Biotechnology Letters, 2008, vol. 30, No. 12 pp. 2045-2052.
Michael et al., "Reduced Accumulation of Specific MicroRNAs in Colorectal Neoplasia", Molecular Cancer Research, 2003, vol. 1, pp. 882-891.
Landgraf et al., "A Mammalian microRNA Expression Atlas Based on Small RNA Library Sequencing", Cell, 2007, vol. 129, pp. 1401-1414.
Lagos-Quintana et al., "Identification of Tissue-Specific MicroRNAs from Mouse", Current Biology, 2002, vol. 12, pp. 735-739.
Neilson et al., "Dynamic regulation of miRNA expression in ordered stages of cellular development", Genes & Development, 2007, vol. 21, pp. 578-589.
Ruby et al., "Large-Scale Sequencing Reveals 21U-RNAs and Additional MicroRNAs and Endogenous siRNAs in *C. elegans*", Cell, 2006, vol. 127, pp. 1193-1207.
Wu et al., "miRNA Profiling of Naïve, Effector and Memory CD8 T Cells", PLoS ONE, 2007, vol. 2, Iss.10, e1020.
Calin et al., "Frequent deletions and down-regulation of micro-RNA genes miR15 and miR16 at 13q14 in chronic lymphocytic leukemia", PNAS, 2002, vol. 99, No. 24, pp. 15524-15529.
Obernosterer et al., "Post-transcriptional regulation of microRNA expression", RNA, 2006, vol. 12, pp. 1161-1167.
Meng et al., "MicroRNA-21 Regulates Expression of the PTEN Tumor Suppressor Gene in Human Hepatocellular Cancer", Gastroenterology, Elsevier, 2007, vol. 133, No. 2, pp. 647-658.
Sui et al., "Microarray analysis of MicroRNA expression in acute rejection after renal transplantation", Transplant Immunology, Elsevier, 2008, vol. 19, No. 1, pp. 81-85.
Bandres et al., "Identification by Real-time PCR of 13 mature microRNAs differentially expressed in colorectal cancer and non-tumoral tissues", Molecular Cancer, Biomed Central, 2006, vol. 5, pp. 29-38.
Ohyashiki et al., "Impact on cell to plasma ratio of miR-92a in patients with acute leukemia: in vivo assessment of cell to plasma ratio of miR-92a", BMC Research Notes, Biomed Central Ltd., 2010, vol. 3, No. 1, pp. 1-8.
Tanaka et al., "Down-regulation of miR-92 in human plasma is a novel marker for acute leukemia patients", PLOS ONE, Public library of Science, 2009, vol. 4, No. 5, pp. E5532.1-E5532.5.
Extended European Search Report dated Oct. 7, 2011 issued in counterpart European Patent Application No. 09738852.4.
Matsubara, H., et al., "Apoptosis induction by antisense oligonucleotides against miR-17-5p and miR-20a in lung cancers overexpressing miR-17-92," Oncogene, 2007, pp. 6099-6105, vol. 26.
Stefano Volinia, et al., "A microRNA expression signature of human solid tumors defines cancer gene targets", PNAS, Feb. 14, 2006, pp. 2257-2261, vol. 103, No. 7.
Yuan-Shuai Huang, et al., "Microarray anaylysis of microRNA expression in hepatocellular carcinoma and non-tumorous tissues without viral hepatitis", Journal of Gastroenterology and Hepatology, 2008, pp. 87-94, vol. 23.
Aurora Esquela-Kerscher, et al., "Oncomirs-microRNAs with a role in cancer", Nature Reviews, Apr. 2006, pp. 259-269, vol. 6.
Office Action issued by the Japanese Patent Office dated Oct. 3, 2013 in counterpart Application No. 2010-510157.
Communication dated Nov. 6, 2013, issued by the European Patent Office in corresponding Application No. 09738852.4.
Volinia et al., "A microRNA expression signature of human solid tumors defines cancer gene targets", PNAS, Feb. 14, 2006, vol. 103, No. 7, pp. 2257-2261.
Tricoli et al., "MicroRNA: Potential for Cancer Detection, Diagnosis, and Prognosis", Cancer Research, American Association for Cancer Research, May 15, 2007, vol. 67, No. 10, pp. 4553-4555.
Lawrie et al., "Detection of elevated levels of tumour-associated microRNAs in serum of patients with diffuse large B-cell lymphoma", British Journal of Haematology, Journal Compilation & Blackwell Publishing Limited, vol. 141, No. 5, pp. 672-675, 2008.
Kemppainen et al., "microRNAs as Biomarkers in Blood and Other Biofluids", Asuragen, Inc., 2007, retrieved from Internet: URL: http://asuragen.de/pdfs/posters/biomarkers.pdf, 1 page total.

* cited by examiner

CANCER MARKER, METHOD FOR EVALUATION OF CANCER BY USING THE CANCER MARKER, AND EVALUATION REAGENT

CROSS REFERENCE TO RELATED APPLICATIONS

This is a Divisional of application Ser. No. 13/472,190, filed May 15, 2012 which is a Divisional of application Ser. No. 12/990,330, filed Jan. 5, 2011, which is a national stage of PCT/JP2009/058421, filed Apr. 28, 2009, claiming priority based on the Japanese Patent Application No. 2008-119280, filed Apr. 30, 2008, the contents of all of which are hereby incorporated herein by reference in their entirety.

TECHNICAL FIELD

The present invention relates to a cancer marker, a method for evaluating the possibility of cancers using the same, and an evaluation reagent. The present invention also relates to a correction marker, correction method, and correction reagent for correcting the cancer marker in the evaluation method.

BACKGROUND ART

In the field of clinical medical practice, it is required to easily judge the presence or absence of a disease, the degree of progression of the disease, the effect obtained after a treatment, etc. Under these circumstances, as a method for judging them indirectly, detecting a marker whose expression amount changes specifically accompanying the onset or progression of each disease has been proposed, and attempts actually are made to put this into practical use.

Among various diseases, detecting malignant tumors, which are so-called cancers, early and selecting and changing a treatment strategy therefor appropriately are particularly important. Thus, in order to realize indirect judgment by the detection of a marker as described above, various cancer markers (tumor markers) have been reported. Specific examples of the cancer marker include PSA (Prostate-Specific Antigen), CEA (Carcinoembryonic Antigen), CA 19-9 (Carcinoembryonic Antigen 19-9), and CA 72-4 (Carcinoembryonic Antigen 72-4). Furthermore, it is described in Non-Patent Documents 1 and 2 that the expression of miRNAs such as has-mir-15, has-mir-16, miR-143, and miR-145 is downregulated in lymphocytic leukemia, colon cancer, and the like (Non-Patent Documents 1, 2).

PRIOR ART DOCUMENTS

Non-Patent Documents

[Non-Patent Document 1] Calin G A, Dumitru C D, Shimizu M et al., Frequent deletions and down-regulation of microRNA genes miR15 and miR16 at 13q14 in chronic lymphocytic leukemia, Proc Natl Acad Sci USA, 2002, vol. 99, pp. 15524-9
[Non-Patent Document 2] Michael M Z, SM O C, van Holst Pellekaan N G, Young G P, James R J, Reduced accumulation of specific microRNAs in colorectal neoplasia, Mol cancer Res, 2003, vol. 1, pp. 882-91

BRIEF SUMMARY OF THE INVENTION

Problem to be Solved by the Invention

However, in the field of clinical medical practice, since cancer markers with which the onset of cancers and their progression can be judged with excellent reliability are necessary, there still is a demand for the provision of a novel cancer marker. Thus, with the foregoing mind, it is an object of the present invention to provide a novel cancer marker for evaluating cancers, an evaluation method using the cancer marker, and an evaluation reagent to be used in the evaluation method. Furthermore, it is another object of the present invention to provide a novel correction marker for correcting the expression level of the cancer marker, a correction method for correcting the expression level using the correction marker, and a correction reagent to be used in the correction method.

Means for Solving Problem

A cancer marker of the present invention is a cancer marker applicable to a cancer other than breast cancer, containing at least one miRNA selected from hsa-miR-92 and hsa-miR-494.

An evaluation method of the present invention is an evaluation method for evaluating a possibility of a cancer other than breast cancer. The evaluation method includes the step of detecting an expression level of a cancer marker in a biological sample. In the evaluation method, the cancer marker is the cancer marker of the present invention.

An evaluation reagent of the present invention is an evaluation reagent for evaluating a possibility of a cancer other than breast cancer. The evaluation reagent contains a miRNA detection reagent for detecting at least one miRNA selected from hsa-miR-92 and hsa-miR-494. The evaluation reagent is used in the evaluation method of the present invention.

A correction marker of the present invention contains hsa-miR-638. The correction marker is used to correct an expression level of the cancer marker of the present invention in a biological sample in the evaluation method of the present invention.

A correction method of the present invention includes, in order to correct an expression level of the cancer marker of the present invention in a biological sample in the evaluation method of the present invention, the steps of:
measuring an expression level of the cancer marker in a biological sample;
measuring an amount of a correction marker expressed in the biological sample; and
correcting the expression level of the cancer marker by setting a ratio between an amount of the cancer marker expressed and the amount of the correction marker expressed to a corrected expression level of the cancer marker in the biological sample.

A correction reagent of the present invention contains a miRNA detection reagent for detecting hsa-miR-638. The correction reagent is used to correct an expression level of the cancer marker of the present invention in a biological sample in the evaluation method of the present invention.

Effects of the Invention

The inventors of the present invention conducted a diligent study, and as a result, they found that the expression levels of hsa-miR-92 and hsa-miR-494 in a biological sample decrease accompanying the development of cancers, thereby achieving the present invention. According to the cancer marker of the present invention, by detecting the expression level thereof in a biological sample, it is possible to judge the presence or absence of cancer development or the cancer progression, for example. Furthermore, the cancer marker of the present invention provides a significant difference between negative and positive regarding the canceration, for example. Thus, according to the cancer marker of the present invention, it becomes possible to detect cancers at an initial stage easily whereas such detection is difficult by general palpation and the like. Still further, according to the correction marker of the present invention, the accuracy of detection using the cancer marker further can be improved.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 1A is a graph showing the signal intensity values of various miRNAs contained in each of the samples, and FIG. 1B is a graph showing a logarithmic value ($\log_{10}$ [individual rank_Normal/Average rank_Normal]) of a value obtained by dividing a signal value rank of each miRNA in each of the samples derived from the seven normal subjects by the signal value average rank thereof.

DETAILED DESCRIPTION OF THE INVENTION

<Cancer Marker>

Figure 1A:
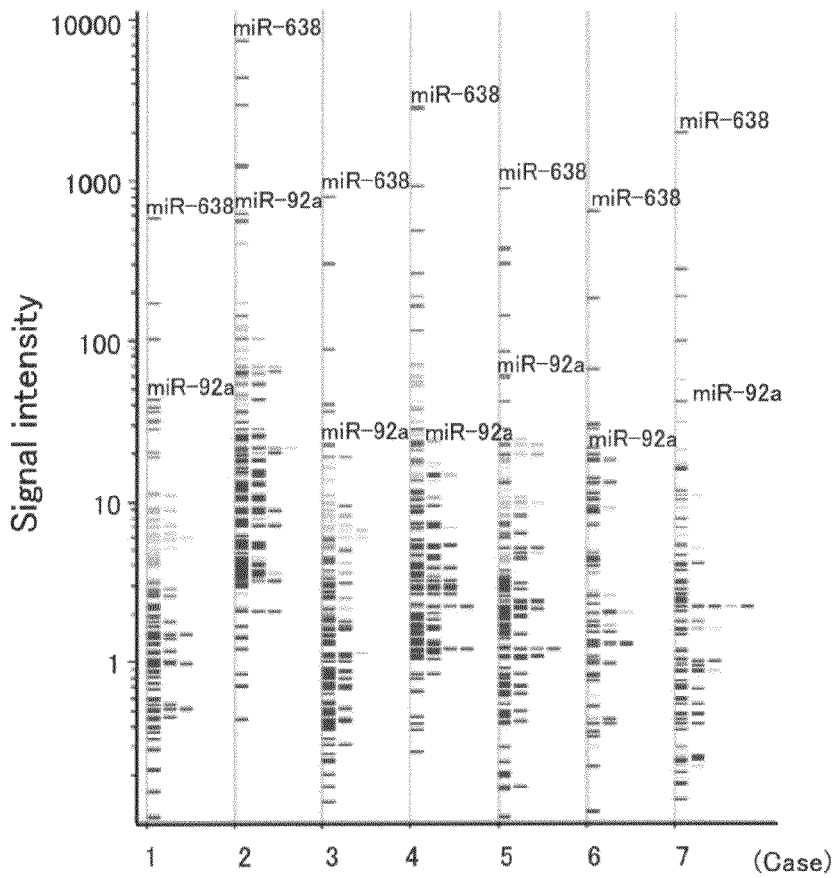
FIGS. 1A and 1B are graphs showing the expression profiles of various miRNAs in samples derived from normal subjects in Example 2 of the present invention.

The cancer marker of the present invention is, as described above, a cancer marker applicable to a cancer other than breast cancer, containing at least one miRNA selected from hsa-miR-92 and hsa-miR-494.

As described above, by the inventors of the present invention, it has been revealed that the expression levels of these miRNAs change specifically accompanying the canceration of cells of various tissues. More specifically, it has been revealed that the expression levels of the miRNAs in, for example, plasma or serum decreases accompanying the canceration. From this fact, it is interpreted that, for example, the expression levels of the miRNAs decrease significantly: after the onset of a cancer as compared with before the onset of the cancer; in the preclinical stage as compared with before the preclinical stage; in the clinical stage as compared with before the clinical stage, in the initial stage as compared with before the initial stage; after the initial stage as compared with in the initial stage. Therefore, by detecting the expression levels of these miRNAs, it becomes possible to carry out evaluation or the like of the possibility that a subject may develop a cancer, whether or not canceration has occurred, the stage of cancer progression such as a preclinical stage (an initial stage) or a clinical stage (an advanced stage or a disease stage), or prognosis, for example.

The meaning of the terms used in the present invention is as follows. The term "cancer" generally means malignant tumor. The term "canceration" generally means the onset of a cancer and also encompasses "malignant transformation". Regarding the term "onset", for example, the time point at which one is diagnosed as having a specific disease through synthetic judgment based on disease-specific clinical symptoms, test data, etc., is referred to as the onset of the disease. The term "preclinical stage" generally refers to a condition before the onset of a disease where disease-specific clinical symptoms have not appeared yet but in an early stage of the disease in which a trace amount of malignant tumor cells are present already. In cervical cancer, the preclinical stage generally indicates precancerous lesions such as CIN1, CIN2, and CIN3. In colon cancer, the preclinical stage indicates a condition of having adenoma. The term "clinical stage" generally refers to cancers found through image findings and cancers that can be identified by the use of existing tumor markers. The term "initial stage" generally indicates a condition of having an early cancer. The term "prognosis" means, for example, a postoperative course of a disease. Since the cancer marker of the present invention can provide useful information for, for example, predicting prognosis, foreseeing the course of a disease, and selecting an appropriate treatment method, it also can be referred to as a "prognostic factor". The "stage of cancer progression" can be judged as appropriate based on, for example, the kind of cancerous tissues or the like. In general, Stage 0 and Stage I can be classified as an initial cancer, Stage II can be classified as an early cancer, and Stage III and Stage IV can be classified as an advanced cancer.

Cancers to which the cancer marker of the present invention is applicable are not particularly limited, and examples thereof include colon cancer, gallbladder cancer, stomach cancer, lung cancer, leukemia, pancreas cancer, prostate cancer, bladder cancer, kidney cancer, uterine body cancer, cervical cancer, hepatocyte cancer, biliary tract cancer, brain tumor, laryngeal cancer, tongue cancer, rectal cancer, and osteosarcoma.

In the present invention, each miRNA may be, for example, a single strand (monomer) or a double strand (dimer). Furthermore, in the present invention, each miRNA preferably is the miRNA in its mature form cleaved by ribonuclease such as Dicer.

In the present invention, the hsa-miR-92 may be, for example, hsa-miR-92a, which preferably is the miRNA in its mature form as described above.

The sequence of the mature hsa-miR-92a is registered under Accession No. MIMAT0000092, for example. This sequence is shown as SEQ ID NO: 1 below.

```
hsa-miR-92a
                                          (SEQ ID NO: 1)
5'-uauugcacuugucccggccugu-3'
```

The hsa-miR-494 may be, for example, the miRNA in its mature form as described above. The sequence of the mature miRNA is registered under Accession No. MIMAT0002816. The sequence of the mature hsa-miR-494 is shown as SEQ ID NO: 2.

```
hsa-miR-494
                                          (SEQ ID NO: 2)
5'-ugaaacauacacgggaaaccuc-3'
```

As disclosed in the documents listed below, the 5' end and the 3' end of each of the miRNAs respectively have some variations, for example. Therefore, each of the miRNAs of the present invention also encompasses variants having a sequence different from the sequence thereof in its mature form by a few bases.

Wu H. et al., 2007, PLoS ONE 2 (10): e1020 miRNA profiling of naive, effector and memory CD8 T cells.

Pablo Landgraf et al., 2007, Cell, vol. 129, pp. 1401-1414 A Mammalian microRNA Expression Atlas Based on Small RNA Library Sequencing.

Neilson et al., 2007, Genes Dev, vol. 21, pp. 578-589 Dynamic regulation of miRNA expression in order to stage of cellular development.

Ruby et al., 2006, Cell, vol. 127, pp. 1193-1207 Large-scale sequencing reveals 21U-RNAs and additional microRNAs and endogeneous siRNAs in C. elegans.

Obernoster et al., RNA 2006 12: pp. 1161-1167 Post-transcriptional regulation of microRNA expression.

Lagos-Quintana et al., 2002, Curr Biol, vol. 12, pp. 735-739 Identification of tissue-specific microRNAs from mouse.

The miRNAs in the present invention encompass, for example, polynucleotides having a base sequence with a homology to the base sequences of the respective SEQ ID NOs: 1 and 2, and polynucleotides having a base sequence complementary thereto. The "homology" refers to the degree of identity between sequences to be compared with each other when they are aligned appropriately, and represents the occurrence ratio (%) of perfect match of amino acids between these sequences. When it is described that the base sequence of a polynucleotide "has a homology" to the base sequences of the miRNAs of the present invention, it means that the polynucleotide is similar enough to the miRNAs to be able to maintain the function as the miRNAs of the present invention. The alignment can be achieved by using an arbitrary algorithm such as BLAST, for example. Even when the base sequences differ from each other by, for example, point mutation, deletion, or addition, it can be said that they are homologous as long as such a difference does not affect the function of the miRNAs. The number of bases different between the base sequences is, for example, 1 to 20, 1 to 15, 1 to 10, 1 to 5, 1 to 3, 1 to 2, or 1. Furthermore, when base sequences of two polynucleotides to be compared with each other have an identity of, for example, 80%, 85%, 90%, 91%, 92%, 93%, 94%, 95%, 96%, 97%, 98%, or about 99%, it can be said that they are homologous. Furthermore, for example, when one of the two polynucleotides hybridizes to a polynucleotide having a base sequence complementary to the other polynucleotide under stringent conditions, it can be said that the two polynucleotides are homologous. The stringent conditions are not particularly limited, and may be such that, for example, the two polynucleotides are kept at a temperature of "Tm−25° C." overnight in a solution containing 6×SSC, 0.5% SDS, 5×Denhardt's solution, and 0.01% denatured salmon sperm nucleic acid.

The cancer marker of the present invention is, for example, a miRNA present in a biological sample. The biological sample in the present invention is a liquid fraction collected from a living organism (e.g., a subject), and examples thereof include blood, saliva, urine, and diluted solutions thereof. Among them, a blood sample is preferable because change in expression levels of the various miRNAs accompanying the canceration is particularly noticeable.

The blood sample is not particularly limited. It may be, for example, a sample containing a liquid fraction of blood, such as a so-called plasma-containing sample or serum-containing sample. Specific examples of the sample include whole blood, a liquid fraction, plasma fraction, and serum fraction of whole blood, samples containing them, and samples obtained by diluting them.

<Evaluation Method>

The evaluation method of the present invention is, as described above, an evaluation method for evaluating a possibility of a cancer other than breast cancer. The evaluation method includes the step of detecting an expression level of a cancer marker in a biological sample. In the evaluation method, the cancer marker is the cancer marker of the present invention.

The present invention is characterized in that the cancer marker of the present invention is detected as a cancer marker, and for example, a method for detecting the expression level of each miRNA is by no means limited. The cancer marker of the present invention is as described above. In the present invention, the cancer marker to be detected may be, for example, either one of hsa-miR-92 and hsa-miR-494 or both of them. When the cancer marker to be detected is hsa-miR-92, it is preferable that the hsa-miR-92 is in its mature form, for example. When the cancer marker to be detected is hsa-miR-92a, it is preferable that the hsa-miR-92a is in its mature form.

In the present invention, cancers to be evaluated are not particularly limited, and as described above, examples thereof include colon cancer, gallbladder cancer, stomach cancer, lung cancer, leukemia, pancreas cancer, prostate cancer, bladder cancer, kidney cancer, uterine body cancer, cervical cancer, hepatocyte cancer, biliary tract cancer, brain tumor, laryngeal cancer, tongue cancer, rectal cancer, and osteosarcoma.

In the present invention, the biological sample is not particularly limited, and examples thereof include, as described above, blood, saliva, and urine. Among them, the biological sample preferably is the above-described blood sample, more preferably a sample containing plasma, a sample containing serum, or the like, because change in expression levels of the various miRNAs accompanying the canceration is particularly noticeable. Such a blood sample is particularly preferable also because, for example, a test can be carried out merely by collecting blood and the pain and burden placed on a subject can be reduced considerably.

The evaluation method of the present invention further may include the step of determining the possibility of the cancer. More specifically, the evaluation method of the present invention may include the step of determining the possibility of the cancer based on the expression level of the cancer marker in the biological sample detected in the cancer marker-detecting step by at least one method selected from the group consisting of methods (1), (2), and (3):

(1) the expression level of the cancer marker in the biological sample of a subject is compared with an expression level of the cancer marker in a biological sample of a normal subject, and when the expression level in the subject is lower than the expression level in the normal subject, it is determined that the subject has a high possibility of the cancer;

(2) the expression level of the cancer marker in the biological sample of a subject is compared with an expression level of the cancer marker in a biological sample of a normal subject, and as the expression level in the subject becomes relatively lower than the expression level in the normal subject, it is determined that the cancer in the subject is relatively advanced; and (3) the expression level of the cancer marker in the biological sample of a subject is compared with an expression level of the cancer marker in a biological sample of each of cancer patients at different progression stages, and it is determined that the cancer in the subject is in the same progression stage as the cancer in the patient exhibiting the same or similar expression level.

In the present invention, the possibility of a cancer encompasses, for example, the possibility that the subject may develop a cancer, whether or not canceration has occurred, the stage of cancer progression such as a preclinical stage or a clinical stage, prognosis, or the like. In the present invention, the term "normal subject" means, for example, a subject who is not judged as having developed a cancer to be evaluated or having a possibility that he has developed the cancer.

The expression level of the cancer marker in the normal subject in the methods (1) and (2) can be determined previously using a biological sample collected from the normal subject, for example. Furthermore, the expression levels of the cancer marker in the cancer patients in the method (3) also can be determined by, for example, previously classifying the patients according to the progression stage and using biological samples collected from the patients at the respective progression stages. In the methods (1) to (3), the kind of the biological samples of the normal subject and the patients preferably are the same as the kind of the biological sample of the subject, for example, and the biological sample preferably is a blood sample, particularly preferably a sample containing plasma or a sample containing serum, for example. Furthermore, the biological samples of the normal subject and the patients preferably are prepared in the same manner and under the same conditions as the biological sample of the subject, for example.

In the present invention, the expression level of the cancer marker may be, for example, the amount of the cancer marker expressed in the biological sample. The amount of the cancer marker expressed may be, for example, the actual amount of miRNA or a value correlated with the actual amount of miRNA. Examples of the latter include a signal value obtained when detecting the miRNA. This signal value can be determined as appropriate depending on, for example, the method for detecting the miRNA and the kind of a detector for detecting the signal value. When the detection method is, for example, a PCR method such as a real-time RT-PCR (real-time reverse transcription-polymerase chain reaction) method, the signal value can be expressed with a unit of copies/μl or the like, for example.

It is preferable that the expression level of the cancer marker is corrected with the expression level of a correction marker, for example. The correction marker is not particularly limited, and may be, for example, a substance exhibiting a constitutive expression level in a biological sample. In particular, the correction marker preferably is a substance exhibiting a constitutive expression level in a biological sample regardless of the presence or absence of canceration. By detecting the expression level of such a correction marker as an internal standard in a biological sample collected to detect the cancer marker, the expression levels of the cancer marker between different subjects and the expression levels in the same subject over time can be compared with still higher reliability, for example. For the reasons stated above, the evaluation method of the present invention further may include the step of detecting the expression level of the correction marker in the biological sample collected from the subject.

The above-described corrected expression level of the cancer marker can be represented as the ratio between the amount of the cancer marker expressed and the amount of the correction marker expressed in the biological sample, for example. Specifically, it can be represented as, for example, "the amount of the cancer marker expressed/the amount of the correction marker expressed" or "the amount of the correction marker expressed/the amount of the cancer marker expressed". The expression of the cancer marker of the present invention decreases accompanying the canceration. Thus, in the case where it is represented as "the amount of the cancer marker expressed/the amount of the correction marker expressed" as the former, for example, it can be judged that the possibility of a cancer becomes higher as the value becomes relatively smaller. On the other hand, in the case where it is represented as "the amount of the correction marker expressed/the amount of the cancer marker expressed" as the latter, it can be judged that the possibility of a cancer becomes higher as the value becomes greater, for example.

The correction marker is not particularly limited, and a known marker can be used as the correction marker. In the present invention, it is preferable to use, in particular, hsa-miR-638 as the correction marker. The correction marker containing this miRNA corresponds to the correction marker of the present invention to be described later, and it exhibits constitutive expression in a biological sample regardless of the presence or absence of canceration, for example. Since the correction marker of the present invention exhibits constitutive expression regardless of the presence or absence of canceration as described above, it can serve as an internal standard in a biological sample.

The correction marker of the present invention, i.e., the hsa-miR-638, preferably is the miRNA in its mature form cleaved by a ribonuclease such as Dicer, for example.

The hsa-miR-638 may be, for example, the miRNA in its mature form as described above. The sequence of the mature miRNA is registered under Accession No. MIMAT00033088. The sequence of the mature hsa-miR-638 is shown as SEQ ID NO: 3.

```
hsa-miR-638
                                            (SEQ ID NO: 3)
5'-agggaucgcgggcggguggcggccu-3'
```

In the present invention, the subject is not particularly limited, and examples thereof include: mammals including humans, dogs, and cats; primates; and rodents.

In the following, the evaluation method of the present invention will be described with reference to an example where plasma or serum is used as a biological sample. It is to be noted, however, the present invention is not limited thereto.

First, total RNA is extracted from plasma or serum of a subject. The plasma or serum can be recovered by a known method, and for example, it can be prepared by collecting whole blood from the subject and removing a blood cell fraction through centrifugation. Furthermore, the method for extracting the total RNA from the plasma or serum is not particularly limited, and any of known methods can be employed. Examples of the extraction method include a guanidine-CsCl ultracentrifugation method and an AGPC (Acid Guanidinium-Phenol-Chloroform) method.

Next, the cancer marker of the present invention, i.e., at least one of hsa-miR-92 and hsa-miR-494, in the extracted total RNA is detected. The method for detecting the cancer marker of the present invention is by no means limited, as long as it can detect the expression of the miRNA as described above. Specific examples of the detection method include, for example, Northern blot analysis, a real-time RT-PCR detection method, and a microarray analysis method. The present invention is characterized in that the miRNA to be detected as a cancer marker is at least one of hsa-miR-92 and hsa-miR-494. A method for detecting it is by no means limited, and those skilled in the art can carry out such a method based on common general technical knowledge.

Northern blot analysis can be carried out, for example, using a probe as described below. The probe is not particularly limited, and probes that can detect the above-described miRNAs can be used. For example, the probe may be the one that can hybridize to any of the above-described miRNAs. A commercially available product may be used as the probe, or the probe may be prepared on your own, for example. The sequence of the probe can be designed as appropriate based on the base sequences of the miRNAs and common general technical knowledge, for example. Specific examples of the probe include the one having a sequence complementary to the miRNA to be detected. It is preferable that the sequence of the probe is, for example, at least about 70% complementary to the miRNA to be detected, more preferably at least 90% complementary to the same, and particularly preferably 100% complementary to the same. The constitutional unit of the probe is not particularly limited, and, for example, a known constitutional unit can be employed. Specific examples of the constitutional unit include nucleotides such as deoxyribonucleotide and ribonucleotide, PNA (Peptide Nucleic Acid), and LNA (Locked Nucleic Acid). Examples of the LNA include BNA (Bridged Nucleic Acid) such as 2',4'-bridged nucleic acid. Bases in the nucleotides are not particularly limited. They may be, for example, natural bases such as adenine, guanine, cytosine, thymine, and uracil, or may be unnatural bases (artificial bases). The length of the probe is not particularly limited, and is, for example, 10 to 100 mer, preferably 10 to 40 mer, more preferably 10 to 25 mer, and still more preferably 15 to 20 mer.

As a specific example, first, the extracted total RNA is fractionated depending on the strand length by electrophoresis, and the fractionated total RNA is transcribed onto a membrane from the gel used in the electrophoresis. Examples of the membrane include a nitrocellulose membrane and a nylon membrane. Subsequently, the membrane on which the fractionated RNAs have been transcribed was incubated in a predetermined buffer in the presence of the above-described probe labeled with a radioactive material such as $^{32}P$. Then, by detecting the label of the probe, miRNA that has hybridized with the probe can be detected. When the probe labeled with a radioactive material is used as described above, the miRNA that has hybridized with the probe can be quantified by, for example, autoradiography, based on the band intensity. Conditions of the Northern blot analysis are not particularly limited, and it is preferable that, for example, prehybridization, hybridization, and washing are carried out under stringent conditions. For example, in the case where DNA labeled with $^{32}P$ is used as a probe, the stringent conditions are at 37° C. in a hybridization buffer. The hybridization buffer may be, for example, a buffer containing 0.25 mol/l sodium phosphate (pH 7.2), 7% SDS, and 0.5% sodium pyrophosphate. Furthermore, in the washing step, the stringent conditions are at 37° C. in a washing buffer containing 2×SSC and 1% SDS and further at room temperature in a washing buffer containing 0.1×SSC. It should be note that the stringent conditions are not limited thereto, and depending on the selected detection method, conditions standard therefor can be employed.

The real-time RT-PCR detection method can be carried out using a fluorescent reagent as described below, for example. First, for example, a linker is ligated to each of 5' end and 3' end of the extracted total RNA. Then, with the total RNA having the linker ligated thereto as a template, cDNA is amplified. Further, with the thus-obtained cDNA as a template, PCR is carried out using a primer that can amplify the miRNA to be detected. The primer is by no means limited, and examples thereof include primers that can hybridize to the above-described miRNA or a peripheral region of the miRNA. The primer can be designed as appropriate based on the base sequence of the above-described miRNA and common general technical knowledge, for example. Specific examples of the primer include a probe having a sequence complementary to the miRNA to be detected or a peripheral region of the miRNA. It is preferable that the sequence of the primer is, for example, at least about 70% complementary to, for example, the miRNA to be detected or a peripheral region of the miRNA, preferably at least 80% complementary to the same, more preferably at least 90% complementary to the same, still more preferably at least 95% complementary to the same, and particularly preferably 100% complementary to the same. The constitutional unit of the primer is not particularly limited, and is, for example, the same as that of the above-described probe. The length of the primer is not particularly limited, and may be a general length.

At the time of carrying out the PCR, it is preferable to cause a fluorescent reagent to be present in a PCR reaction solution, for example. Examples of the fluorescent reagent include a fluorescent dye that specifically binds to a double-stranded nucleic acid and a fluorescent dye that intercalates into a double-stranded nucleic acid. When such a fluorescent reagent forms a double-stranded nucleic acid by nucleic acid amplification, the fluorescent dye binds to or intercalates into the double-stranded nucleic acid. Then, by measuring the fluorescence intensity of the fluorescent dye that has bound to or intercalated into the double-stranded nucleic acid, it is possible to quantify the miRNA to be detected. Examples of the fluorescent dye include SYBR (trademark) Green. Such a real-time RT-PCR detection method can be carried out by a known method, for example. Also, it can be carried out, for example, using a commercially available reagent such as SYBR (trademark) Green PCR Master Mix (trade name, Perkin-Elmer Applied Biosystems) and a commercially available detector such as ABI Prism 7900 Sequence Detection System (trade name, Perkin-Elmer Applied Biosystems) in accordance with their manuals. Furthermore, the above-described primer also may serve as the fluorescent reagent. Such a primer may be, for example, a labeled primer labeled with a fluorescent dye, whose fluorescence is quenched when a fluorescent double-stranded nucleic acid has not yet been formed and the quenching is released when the double-stranded nucleic acid is formed. Such a labeled primer can be designed based on common general technical knowledge, for example.

When the expression amount is measured by such a detection method, it is preferable that an internal standard such as a correction marker is measured, and with regard to the miRNA to be detected, the expression amount corrected with the internal standard is calculated as will be described later, for example.

On the other hand, the cancer marker of the present invention in plasma or serum collected from a normal subject also is detected in the same manner. At this time, it is preferable that the kind of the cancer marker used for the subject is the same as that used for the normal subject. It is preferable that the expression level of the cancer marker of the present invention in the normal subject is determined previously, for example, and it is not necessary to determine the expression level in the normal subject every time evaluation is made. That is, it is preferable that the previously detected expression level of the cancer marker of the present invention in the normal subject is set to a standard value of the normal subject. The expression level in the normal subject may be, for example, a value obtained from a single normal subject or may be a value calculated from the expression levels in a plurality of normal subjects by a statistical method.

Then, from the expression level in the subject and the expression level in the normal subject, the possibility of a cancer in the subject can be evaluated by, for example, the following method (1) or (2).

In the method (1), for example, the expression level of the cancer marker in the subject is compared with the expression level of the cancer marker in the biological sample of the normal subject, and when the expression level in the subject is significantly lower than the expression level in the normal subject, it is determined that the possibility of the cancer is high. As described above, the expression level of the cancer marker of the present invention in blood decreases accompanying the canceration, for example. Therefore, when the expression level in the subject is equal to or higher than that in the normal subject, it can be judged that the subject has a low possibility of canceration. On the other hand, when the expression level in the subject is lower than that in the normal subject, it can be judged that the subject has a high possibility of canceration.

In the method (2), for example, the expression level of the cancer marker in the subject is compared with the expression level of the cancer marker in the biological sample of a normal subject, and when the expression level in the subject becomes relatively lower than the expression level in the normal subject, it is determined that the cancer in the subject is relatively advanced. As described above, the expression level of the cancer marker of the present invention in blood decreases accompanying the progression of canceration, for example. Therefore, as the expression level in the subject is lower than the expression level in the normal subject and the difference in expression level between the subject and the normal subject is relatively small, it can be judged that the cancer progression is less severe, and as the above-described difference is relatively large, it can be judged that the cancer progression is severe.

In the methods (1) and (2), for example, when the expression level in the subject is at least 50% lower than the expression level in the normal subject, for example, it can be judged that the subject has a high possibility of the cancer, and as the expression level in the subject decreases further to be at least 85%, at least 90%, and at least 95% lower than the expression level in the normal subject, it can be judged that the cancer is advanced further. The same applies to the case where the expression level is corrected with a correction marker as will be described later.

Furthermore, instead of or in addition to the detection of the cancer marker with regard to the normal subject, the cancer marker of the present invention may be detected in the same manner with regard to serum or plasma collected from cancer patients at different progression stages. At this time, it is preferable that the kind of the cancer marker used for the subject is the same as that used for the cancer patients. The expression levels of the cancer marker of the present invention in the patients preferably are determined previously, and it is not necessary to determine the expression levels in the patients every time evaluation is made. That is, it is preferable that the previously detected expression level of the cancer marker of the present invention in each cancer patient is set to a standard value for each progression stage. Note here that the expression level in the cancer patient may be a value obtained from, for example, a single cancer patient, or may be a value calculated from the expression levels in a plurality of cancer patients by a statistical method.

Then, from the expression level in the subject and the expression level in each cancer patient, the possibility of the cancer in the subject can be evaluated by, for example, the following method (3).

In the method (3), for example, the expression level of the cancer marker in the subject is compared with the expression level of the cancer marker in the biological sample of each of the cancer patients at different progression stages, and it is determined that the cancer in the subject is in the same progression stage as the cancer in the patient exhibiting the same or similar expression level. As described above, the expression level of the cancer marker of the present invention in blood decreases with the progression of canceration. Therefore, by determining the expression level in the cancer patients at different progression stages, not only the possibility of canceration of the subject but also the progression stage of the cancer can be evaluated through comparison with the thus-determined expression levels.

As described in the methods (1) to (3), when comparing the expression level in the subject with that of the normal subject or each of the cancer patients, the significant difference therebetween can be judged by a statistical method such as a t-test, an F-test, or a chi-square test, for example.

Furthermore, in order to improve the reliability of the evaluation method of the present invention, the evaluation may be carried out using the expression level of the cancer marker of the present invention corrected as described above.

As described above, the corrected expression level can be represented as the ratio between the amount of the cancer marker expressed and the amount of the correction marker expressed in a biological sample, for example. As a specific example, it can be represented as "the amount of the cancer marker expressed/the amount of the correction marker expressed". In the method (1) or (2), the ratio calculated with regard to the subject may be compared with the ratio calculated with regard to the normal subject, for example. Furthermore, in order to make the comparison of these ratios easier, it is preferable that, assuming the ratio calculated with regard to the normal subject is "1", a relative value of the ratio calculated with regard to the subject compared to this is determined, for example. This allows the judgment to be made more easily based on whether the calculated value with regard to the subject is smaller or greater than "1". Furthermore, also in the method (3), for example, the ratio calculated with regard to the subject may be compared with the ratio calculated with regard to each of the cancer patients at the different progression stages.

According to such an evaluation method, for example, with regard to a subject having a cancer at a preclinical stage, it is possible to judge that the subject has a high possibility of the cancer with high reliability whereas such judgment has been difficult conventionally. Furthermore, for example, the stage of cancer progression also can be judged with high reliability. Thus, in prevention or treatments of cancers, information important in determining strategies for medication, operation, etc. for example, can be obtained with high reliability.

<Evaluation Reagent>

The evaluation reagent of the present invention is, as described above, an evaluation reagent to be used in the evaluation method of the present invention and characterized in that it contains a reagent for detecting the cancer marker of the present invention, i.e., a miRNA detection reagent for detecting at least one miRNA selected from hsa-miR-92 and hsa-miR-494. According to such an evaluation reagent, it is possible to carry out the evaluation method of the present invention conveniently.

The present invention is characterized in that, as described above, at least one of hsa-miR-92 and hsa-miR-494 is detected as a cancer marker, and a method for detecting these miRNAs is by no means limited. Therefore, it is only necessary that the miRNA detection reagent contained in the evaluation reagent of the present invention can detect either of these miRNAs, and for example, the kind, composition, etc. of the reagent are by no means limited. Furthermore, those skilled in the art can set detection reagents for these miRNAs based on common general technical knowledge.

The evaluation reagent of the present invention further may contain any of various enzymes, buffer solutions, washing solutions, dissolving solutions, dispersions, diluents and the like, for example, depending on various detection methods. Furthermore, the form of the evaluation reagent of the present invention is not particularly limited. For example, it may be a wet-type reagent in the liquid form or a dry-type reagent in the dry form.

The miRNA detection reagent is not particularly limited, and examples thereof include reagents to be used in the Northern blot analysis and real-time RT-PCR detection method described above. Specific examples of the miRNA detection reagent to be used in the Northern blot analysis include labeled probes that can hybridize to either of these miRNAs, such as those described above. Furthermore, specific examples of the reagent to be used in the real-time RT-PCR detection method include primers for amplifying cDNA from total RNA, primers for amplifying either of these miRNAs, fluorescent reagents that specifically bind to or intercalate into double-stranded nucleic acids, and various reagents that can be used in nucleic acid amplification, such as those described above. Examples of the various reagents include nucleotide triphosphate (dNTP) and enzymes such as DNA polymerase.

<Evaluation Kit>

The evaluation kit of the present invention is, as described above, an evaluation kit to be used in the evaluation method of the present invention and characterized in that it includes a miRNA detection reagent for detecting at least one miRNA selected from hsa-miR-92 and hsa-miR-494 (e.g., the evaluation reagent of the present invention). According to such an evaluation kit, the evaluation method of the present invention can be carried out conveniently. In the evaluation kit of the present invention, the evaluation reagent of the present invention is as described above, for example.

It is preferable that the evaluation kit of the present invention further includes a correction marker detection reagent for detecting a correction marker. The correction marker detection reagent is not particularly limited, and can be determined as appropriate depending on the kind of the correction marker, the method for detecting the correction marker, etc. described above. As described above, the correction marker used in the evaluation method of the present invention preferably is the correction marker of the present invention. Thus, the correction marker detection reagent preferably is a reagent for detecting the correction marker of the present invention, i.e., a miRNA detection reagent for detecting hsa-miR-638, for example. This miRNA detection reagent is not particularly limited. As in the case of the reagent for detecting the cancer marker of the present invention, examples of the miRNA detection reagent include reagents to be used in the Northern blot analysis and the real-time RT-PCR detection method.

The form of the evaluation kit of the present invention is not particularly limited. It may be a wet-type kit in the liquid form or a dry-type kit in the dry form. Various reagents in the evaluation kit of the present invention may be provided separately and used together when the kit is used, or may be mixed together before the kit is used, for example.

The evaluation kit of the present invention may be, for example, a test tool in which the above-described evaluation reagent of the present invention and other various reagents are arranged. The form of the test tool is not particularly limited, and examples of the test tool include reactors such as a microreactor, chips such as a microchip, plates such as a microtiter plate, and arrays such as a microarray. According to such a test tool, for example, by detecting a necessary signal with various kinds of existing detectors such as a real-time PCR device, the evaluation method of the present invention can be carried out easily. Furthermore, the test tool may include, for example, a system for carrying out the following operations by computer processing: numerical conversion of a detected signal; correction of a measured signal value by the expression level of the correction marker as described above; creation of a data file for each subject; storage of the data file in a predetermined directory; statistical analysis of measurement results obtained as to subjects, normal subjects, and patients; and the like. Those skilled in the art can design such a data processing system from existing techniques, methods, and procedures based on common general technical knowledge.

The evaluation kit of the present invention further may include, for example, any of various appliances and the like that can be used to carry out the evaluation method of the present invention. Furthermore, it is preferable that the evaluation kit of the present invention further include instructions for use, for example.

<Correction Marker>

As described above, the correction marker of the present invention contains hsa-miR-638 and is characterized in that it is used to correct the expression level of the cancer marker of the present invention in a biological sample in the evaluation method of the present invention.

The inventors of the present invention conducted a diligent study in order to obtain a novel correction marker that serves as an internal standard in a biological sample. As a result, they found out that the above-described hsa-miR-638 exhibits constitutive expression in a biological sample, in particular, in a blood sample, thus achieving the present invention. miRNA that serves as a correction marker has not yet been reported, and the miRNAs found by the inventors of the present invention are the first such miRNA reported. According to such a correction marker, for example, the comparison as to the cancer marker of the present invention to be detected between subjects or in the same subject over time can be carried out more reliably. The miRNA in the correction marker of the present invention is as described above.

The correction marker of the present invention is a miRNA present in a biological sample, and the biological sample is not particularly limited. The biological sample is not particularly limited, and examples thereof include, as described above, blood, saliva, and urine. Among them, the blood samples as described above are preferable because the expression of the correction marker therein remains constitutive regardless of whether the subject has a cancer or not. Among the blood samples, for example, a sample containing plasma, a sample containing serum, a sample containing plasma and serum, and the like are more preferable.

The correction marker of the present invention can be used to correct the expression level of a marker to be detected in a biological sample. Specifically, the correction marker of the present invention preferably is used to correct the expression level of the cancer marker of the present invention. The correction marker of the present invention is present constitutively regardless of whether the subject has a cancer or not, for example. Accordingly, the kind of the marker to be detected is not limited to the cancer marker of the present invention. For example, it may be a cancer marker whose expression level changes accompanying the onset of a cancer. Note here that the marker to be detected may be, for example, a marker whose expression level in a biological sample varies depending on a disease.

<Correction Method by Correction Marker>

As described above, in order to correct the expression level of the cancer marker of the present invention in a biological sample in the evaluation method of the present invention, the correction method of the present invention includes the steps of:

measuring the expression level of the cancer marker of the present invention in a biological sample;

measuring the amount of the correction marker expressed in the biological sample; and correcting the expression level of the cancer marker by setting the ratio between the amount of the cancer marker expressed and the amount of the correction marker expressed to a corrected expression level of the cancer marker in the biological sample.

According to the correction method of the present invention, since the correction marker is present constitutively in a biological sample, by correcting the expression level of the cancer marker of the present invention in a biological sample with this correction marker, it becomes possible to compare, for example, the expression levels of the cancer marker between different subjects, the expression levels in the same subject over time, etc. with still higher reliability.

It is to be noted that, as described above, the correction method using the correction marker of the present invention can be used not only for the cancer marker of the present invention but also for other markers to be detected in a biological sample, for example. Since the correction marker is present constitutively regardless of whether the subject has a cancer or not, for example, the marker to be detected preferably is a cancer marker whose expression level changes accompanying the onset of a cancer. Specific examples such a cancer marker include, in addition to the cancer marker of the present invention, for example, miR-16-1-15a, miR-145, let-7 family, miR-155, miR-17-92 cluster, miR-21, miR-221, miR10-b, miR-128, miR-181a, miR-181b, miR-125b, miR-145, miR-143, miR-133b, miR-31, miR-135b, miR-96, miR-183, miR-18, miR-224, miR-199a, miR-195, miR-200a, miR-125a, miR-122, miR-126, miR-21, miR-205, miR-15a, miR-16-1, miR-150, miR-222, miR-103, miR-107, miR-204, miR-372, miR-373, miR-146b, miR-197, and miR-346.

The present invention is characterized in that the amount of the cancer marker of the present invention expressed is corrected by the correction marker of the present invention. Thus, methods for measuring the amount of the cancer marker of the present invention expressed and the amount of the correction marker of the present invention expressed are by no means limited. For the correction marker of the present invention, for example, the method may be any method that can detect each miRNA as described above, as in the case of the cancer marker of the present invention.

<Correction Reagent>

As described above, the correction reagent of the present invention includes a miRNA detection reagent for detecting hsa-miR-638 and is characterized in that it is used to correct the expression level of the cancer marker of the present invention in a biological sample in the evaluation method of the present invention. According to such a correction reagent, the correction method of the present invention can be carried out conveniently.

The present invention is characterized in that, as described above, hsa-miR-638 is detected as a correction marker, and a method for detecting the miRNA is by no means limited. Therefore, it is only necessary that the miRNA detection reagent contained in the correction reagent of the present invention can detect this miRNA as described above, and for example, the kind, composition, etc. of the reagent are by no means limited. Furthermore, those skilled in the art can set a miRNA detection reagent for detecting this miRNA as appropriate based on common general technical knowledge.

The correction reagent of the present invention may contain any of various enzymes, buffer solutions, washing solutions, dissolving solutions, dispersions, diluents, and the like, for example, depending on various detection methods for detecting the miRNA. Furthermore, the form of the correction reagent of the present invention is not particularly limited. For example, it may be a wet-type reagent in the liquid form or a dry-type reagent in the dry form.

The miRNA detection reagent is not particularly limited, and examples thereof include reagents to be used in the Northern blot analysis and real-time RT-PCR detection method described above. Specific examples of the miRNA detection reagent to be used in the Northern blot analysis include labeled probes that can hybridize to either of these miRNAs, such as those described above. Furthermore, specific examples of the reagent to be used in the real-time RT-PCR detection method include primers for amplifying cDNA from total RNA, primers for amplifying either of these miRNAs, fluorescent reagents that specifically bind to or intercalate into double-stranded nucleic acids, and various reagents that can be used in nucleic acid amplification, such as those described above. Examples of the various reagents include nucleotide triphosphate (dNTP) and enzymes such as DNA polymerase.

EXAMPLES

Next, the present invention will be described with reference to examples. It is to be noted, however, the present invention is by no means limited by the following examples.

Example 1

Bloods were collected from a normal subject and cancer patients shown in the following tables, and a fraction containing serum and plasma (hereinafter referred to as a sample) was separated from each blood. From the thus-obtained sample, total RNA was extracted using Isogen-LS (trade name) (NIPPON GENE CO., LTD.), and the concentration of the total RNA was adjusted so as to be 100 ng/μl. Then, the total RNA was dephosphorylated using alkaline phosphatase derived from calf small intestine (trade name "Alkaline Phosphatase (Calf intestine) (CIAP)", TAKARA BIO INC.). Thereafter, the total RNA was labeled with a cyanine dye using ligase (trade name "T4 RNA Ligase (Cloned)", Ambion). Note here that these operations were carried out using a kit (trade name "miRNA Labeling Reagent and Hybridization Kit", catalog No. 5190-0408, Agilent Technologies, Inc.) in accordance with a protocol attached thereto. Furthermore, using a microarray slide (trade name "Human miRNA Microarray kit 8×15K V2", catalog No. G4470B, Agilent Technologies, Inc.), hybridization of the cyanine labeled total RNA was caused, and signals were scanned using a scanner (trade name "DNA Microarray Scanner", Agilent Technologies, Inc.). For the signal detection, software programs "Feature Extraction 9.5.3 Software and Agilent Scan Control Software (ver.7.0)" accompanying the scanner were used.

In the above-described manner, signal values indicating the expression levels of hsa-miR-92a and hsa-miR-494 as the cancer markers and hsa-miR-638 as the correction marker in the sample of each of the subjects were obtained. Still further, with regard to each subject, the following (A) and (B) were calculated.
(A) the ratio between the expression level of the cancer marker and the expression level of the correction marker, represented by the following formulae:
hsa-miR-92a/hsa-miR-638 (hereinafter, "92a/638")
hsa-miR-494/hsa-miR-638 (hereinafter, "494/638")
(B) a relative value obtained by dividing the ratios "92a/638" and "494/638" of each of the subjects respectively by ratios "92a/638" and "494/638" of the normal subject (BS63), represented by the following formulae:
[subject 92a/638]/[normal subject 92a/638] (hereinafter, "92a/638/B563") [subject 494/638]/[normal subject 494/638] (hereinafter, [494/638/B563])

The results thereof are shown in Table 1 and Table 2 below, respectively. Table 1 shows the result obtained when the cancer marker was hsa-miR-92a and the correction marker was hsa-miR-638. Table 2 shows the result obtained when the cancer marker was hsa-miR-494 and the correction marker was hsa-miR-638.

by detecting the cancer marker of the present invention, the presence or absence of canceration can be judged with high reliability.

Example 2

Bloods were collected from acute myelogenous leukemia (AML) patients (n=2) and normal subjects (n=7), and a fraction containing serum and plasma (hereinafter referred to as a "sample") was recovered by centrifuging each of the bloods at 15,680 m/s$^2$ for 15 minutes. Except that the thus-obtained samples were used, the expression of miRNAs in each sample was analyzed by microarray analysis in the same manner as in Example 1. Then, with regard to each of the samples derived from the normal subjects, the signal value ranks (Individual rank_Normal) of the various miRNAs expressed were determined, and also the signal value average ranks (Average rank_Normal) of the various miRNAs among the samples derived from the normal subjects were determined. Furthermore, in order to examine the variation in expression of each miRNA among the samples, the signal value rank of each of

TABLE 1

| | Subject | | | | | |
| | Normal subject | Cancer patient | | | | |
| No. | BS63 | BS51 | BS53 | BS55 | BS58 | BS62 |
| --- | --- | --- | --- | --- | --- | --- |
| Sex | woman | woman | man | woman | man | woman |
| Disease | normal | colon cancer | gallbladder cancer | stomach cancer (sm2) | colon cancer (mac) | stomach Ca |
| has-miR-92a | 318.97 | 359.199 | 294.319 | 25.146 | 928.489 | 258.925 |
| hsa-miR-638 | 2317.28 | 59098 | 3215.28 | 8209.97 | 16700.4 | 25753.2 |
| 92a/638 | 0.138 | 0.006 | 0.092 | 0.003 | 0.056 | 0.01 |
| 92a/638/BS63 | 1.000 | 0.044 | 0.665 | 0.022 | 0.404 | 0.073 |

TABLE 2

| | Subject | | | | | |
| | Normal subject | Cancer patient | | | | |
| No. | BS63 | BS51 | BS53 | BS55 | BS58 | BS62 |
| --- | --- | --- | --- | --- | --- | --- |
| Sex | woman | woman | man | woman | man | woman |
| Disease | normal | colon cancer | gallbladder cancer | stomach cancer (sm2) | colon cancer (mac) | stomach Ca |
| hsa-miR-494 | 23.145 | 39.2726 | 2.74749 | 2.48419 | 13.6667 | 14.2209 |
| hsa-miR-638 | 2317.28 | 59098 | 3215.28 | 8209.97 | 16700.4 | 25753.2 |
| 494/638 | 0.010 | 0.001 | 0.001 | 0 | 0.001 | 0.001 |
| 494/638/BS63 | 1.000 | 0.067 | 0.086 | 0.03 | 0.082 | 0.055 |

As can be seen from Table 1, it was found that, when hsa-miR-92a was detected as the cancer marker and corrected with hsa-miR-638 as the correction marker, the expression levels 92a/638/BS63 in the cancer patients were from 0.022 to 0.665, which were much lower than "1.0" as the expression level 92a/638/BS63 in the normal subject. Also, as can be seen from Table 2, it was found that, when hsa-miR-494 was detected as the cancer marker and corrected with hsa-miR-638 as the correction marker, the expression levels 494/638/BS63 in the cancer patients were from 0.03 to 0.086, which were much lower than "1.0" as the expression level 494/638/BS63 in the normal subject. These results demonstrate that, the various miRNAs in each of the samples derived from the normal subjects was divided by the signal value average rank of the corresponding miRNA among the samples derived from the normal subjects, and the logarithm thereof ($\log_{10}$ [individual rank_Normal/Average rank_Normal]) was determined (The base was 10).

Figure 1B:
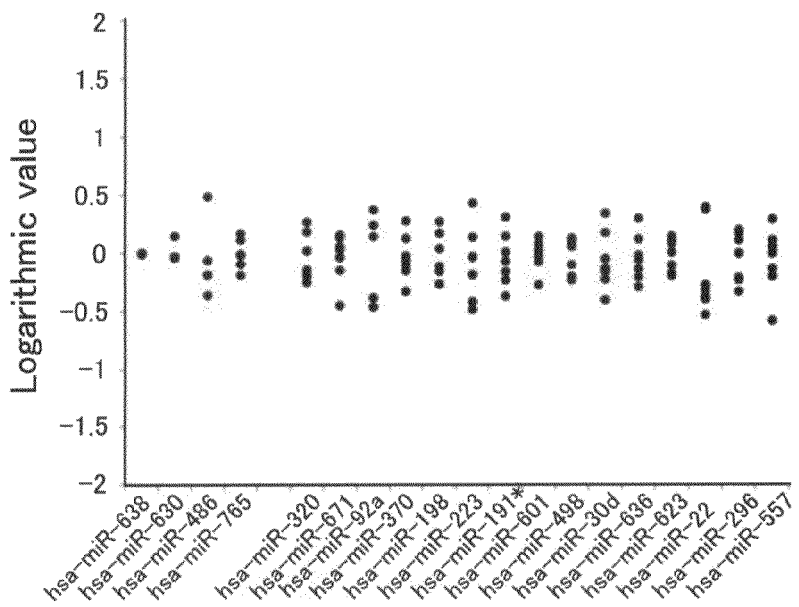

Using these results, first, with regard to the samples prepared from seven specimens derived from the normal subjects, expression profiles of various miRNAs were compared with each other. The result thereof is shown in FIGS. 1A and 1B. FIG. 1A shows the signal intensity values of the various miRNAs contained in each of the samples prepared from the seven specimens. In FIG. 1A, 1 to 7 on the horizontal axis indicate the respective specimens, and the vertical axis indicates the signal intensity. In FIG. 1A, "hsa-miR" is represented by "miR" (hereinafter the same). FIG. 1B shows a logarithmic value ($\log_{10}$ [individual rank_Normal/Average rank_Normal]) of a value obtained by dividing the rank of each of the various miRNAs in the seven normal subjects by the average rank thereof. In FIG. 1B, the horizontal axis indicates the respective miRNAs, and the vertical axis indicates the logarithmic value.

As a result, as can be seen from FIG. 1A, in any of the samples prepared from the seven specimens derived from the normal subjects, expression of hsa-miR-638 and hsa-miR-92a was observed, and further, it was found that hsa-miR-638 exhibited the highest expression level. Furthermore, as can be seen from FIG. 1B, with regard to hsa-miR-638, the above-described logarithmic value regarding the signal value rank was 0. The absolute value of this logarithmic value varies greatly about 0 as the difference in behavior of the expression profile of the miRNA among the respective samples of the normal subjects becomes noticeable, for example.

However, since this logarithmic value was "0" with regard to hsa-miR-638, it was found that hsa-miR-638 exhibits similar expression profile in any of the samples of the normal subjects. These results demonstrate that hsa-miR-638 serves as a correction marker in quantification of miRNA in a sample.

Figure 2:
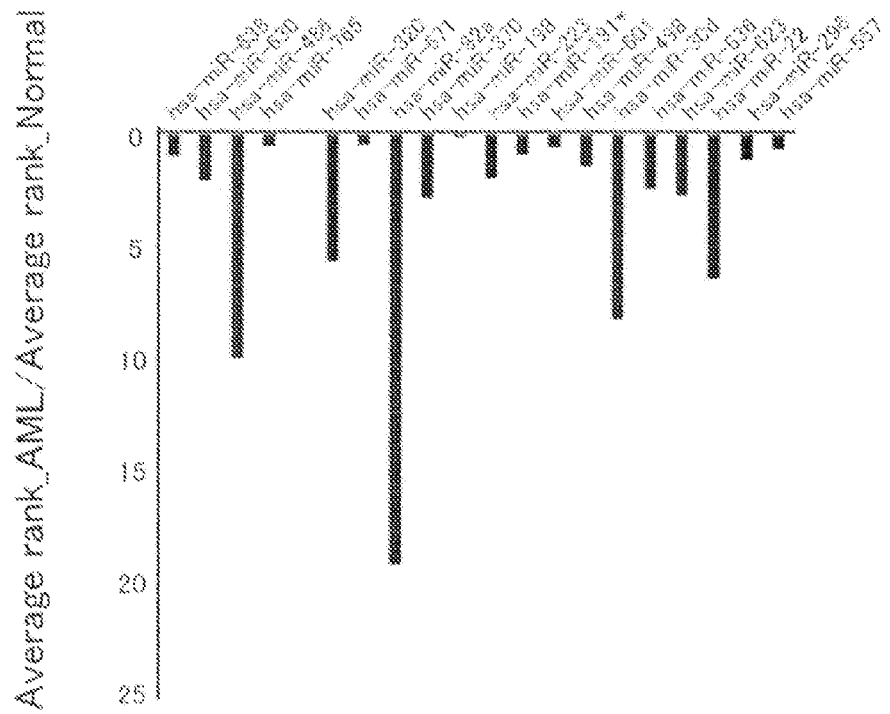
FIG. 2 is a graph showing the ratio (Average rank_AML/Average rank_Nomal) between the signal value average rank of each miRNA between the samples derived from the AML patients and the signal value average rank of each miRNA among the samples derived from the normal subjects in Example 2 of the present invention.

Next, with regard to the samples derived from the AML patients, the signal value average ranks (Average rank_AML) of the various miRNAs between the samples were determined. Then, the signal value average rank (Average rank_AML) of each of the various miRNAs between the samples derived from the two AML patients was divided by the signal value average rank (Average rank_Normal) of each of the various miRNAs among the samples derived from the seven normal subjects to compare the expression profiles of the various miRNAs in the samples derived from the AML patients. The result thereof is shown in FIG. 2. FIG. 2 is a graph showing the ratio (Average rank_AML/Average rank_Normal) between the signal value average rank of each miRNA between the samples derived from the AML patients and the signal value average rank of each miRNA among the samples derived from the normal subjects. As the value of this ratio becomes greater, it means that the difference in expression profile is noticeable between the patients and the normal subjects. In FIG. 2, the vertical axis indicates Average rank_AML/Average rank_Normal, and the horizontal axis indicates the respective miRNAs.

As can be seen from FIG. 2, the signal value average rank of hsa-miR-92a in the AML patients was about 20 times greater than that of hsa-miR-92a in the normal subjects. This indicates that the expression of hsa-miR-92a decreased markedly in the AML patients. This result demonstrates that hsa-miR-92a can serve as a cancer marker for AML.

Example 3

From each of 77 subjects consisting of 39 men and 38 women, a fraction containing plasma and serum (hereinafter referred to as a "sample") was recovered in the same manner as in Example 2. Among these subjects, 16 subjects were normal subjects and 61 subjects were acute leukemia patients. The FAB classification of the acute leukemia patients is as follows:

| AML M0 | 2 (3.2%) |
|---|---|
| AML M1 | 11 (18.0%) |
| AML M2 | 19 (31.1%) |
| AML M3 | 10 (16.3%) |
| AML M4 | 3 (4.9%) |
| AML M4E | 1 (1.6%) |
| AML M5 | 1 (1.6%) |
| AML M5b | 1 (1.6%) |
| AML M6 | 1 (1.6%) |
| AML M7 | 2 (3.2%) |
| AML (with multilineage dysplasia) | 3 (4.9%) |
| ALL L2 | 2 (3.2%) |
| ALL ph+ | 1 (1.6%) |
| ALL preB | 4 (6.5%) |

The expression levels of hsa-miR-92a and hsa-miR-638 in each of the samples were analyzed by quantitative RT-PCR using a commercially available TaqMan (trademark) MicroRNA Assay (Applied Biosystems). Unless otherwise stated, the analysis was conducted in accordance with the instructions for use accompanying the commercially available reagent used.

First, the total RNA was isolated from the sample derived from each of the subjects in the same manner as in Example 2. With 20 ng of the total RNA as a template, a reverse transcription reaction was carried out using "TaqMan (trademark) MicroRNA RT Kit" (trade name) (Applied Biosystems). Specifically, 20 ng of the total RNA (input RNA) were added to 15 µl of a reverse transcription reaction solution having the following composition, and the resultant mixture was incubated at 16° C. for 30 minutes, at 42° C. for 30 minutes, and at 85° C. for 5 minutes, thereby causing a reverse transcription reaction. Note here that, in the following reaction solution, the following primer for hsa-miR-92a and primer for hsa-miR-638 were both miRNA-specific stem-loop primers (Looped RT primers). Specifically, as the following primer for hsa-miR-92a, Assay Name hsa-miR-92, Product number 4373013 of TaqMan (trademark) MicroRNA Assay (Applied Biosystems) was used, and as the primer for hsa-miR-638, Assay Name hsa-miR-638, Product number 4380986 of TaqMan (trademark) MicroRNA Assay (Applied Biosystems) was used.

TABLE 3

| (Reverse Transcription Reaction Solution) | |
|---|---|
| 10 × RT buffer*[1] | 1.5 µl |
| 100 mmol/l dNTPs containing dTTP | 0.15 µl |
| 20 units/µl RNase inhibitor*[1] | 0.188 µl |
| 50 units/µl reverse transcriptase*[2] | 1 µl |
| Primer for hsa-miR-92a | 1 µl |
| Primer for hsa-miR-638 | 1 µl |
| Input RNA | 10.16 µl |
| Total | 15 µl |

*[1]trade name "TaqMan (trademark) MicroRNA RT Kit" (Applied Biosystems)
*[2]trade name "MultiScribe (trademark) Reverse Transcriptase (Applied Biosystems)

Subsequently, with a transcription product obtained through the reverse transcription reaction as a template, quantitative real-time PCR was carried out using Mx3005P (trademark) QPCR system (STRATAGENE). As the reverse transcription product, 1 µl of diluted solution of the reverse transcription product obtained by mixing the reaction solution after the above-described reverse transcription reaction and nuclease-free water at a ratio of 1:2 (volume ratio) was used. Specifically, 20 µl of a PCR reaction solution having the following composition to which 1 µl of the diluted solution had been added was treated at 95° C. for 2 minutes and then was subjected to 50 cycles of incubation with a treatment at 95° C. for 15 seconds and 60° C. for 1 minute as one cycle. In the following PCR reaction solution, the following buffer contained a primer set included in the above-described TaqMan (trademark) MicroRNA Assay (Assay Name hsa-miR-92: Product number 4373013: Applied Biosystems) for hsa-miR-92a detection and TaqMan (trademark) Probe. Alternatively, the buffer contained a primer set included in the above-described TaqMan (trademark) MicroRNA Assay (Assay Name hsa-miR-638: Product number 4380986: Applied Biosystems) for hsa-miR-638 detection and TaqMan (trademark) Probe. In the probe for detecting hsa-miR-92a and the probe for detecting hsa-miR-638, the 5' end was labeled with FAM and the 3' end was labeled with TAMRA.

TABLE 4

(PCR Reaction Solution)

| | |
|---|---|
| 20 × PCR buffer*[1] | 1 µl |
| diluted solution of reverse transcription product | 1 µl |
| TaqMan (trademark) reagent*[2] | 10 µl |
| nuclease-free water | 8 µl |
| Total | 20 µl |

*[1]trade name "TaqMan (trademark) MicroRNA Assays" (Applied Biosystems)
*[2]2 × TaqMan (trademark) Universal Master (Applied Biosystems) MixAmpErase (trademark) UNG (Applied Biosystems) was not added Data obtained through the quantitative RT-PCR was analyzed with MxPro-Mx3005P (trademark) version 3.00 (STRATAGENE), and the automatic Ct setting for baseline adaptation and threshold for Ct determination also were conducted. Then, with regard to the sample derived from each subject, the ratio (hsa-miR-92a/hsa-miR-638) between the fluorescence intensity indicating hsa-miR-92a as the cancer marker and the fluorescence intensity indicating hsa-miR-638 as the correction marker was determined. Furthermore, the Mann-Whitney U test was conducted to examine the statistical significance of the difference between the ratios determined from the samples derived from the normal subjects and the ratios determined from the samples derived from the acute leukemia patients.

Figure 3:
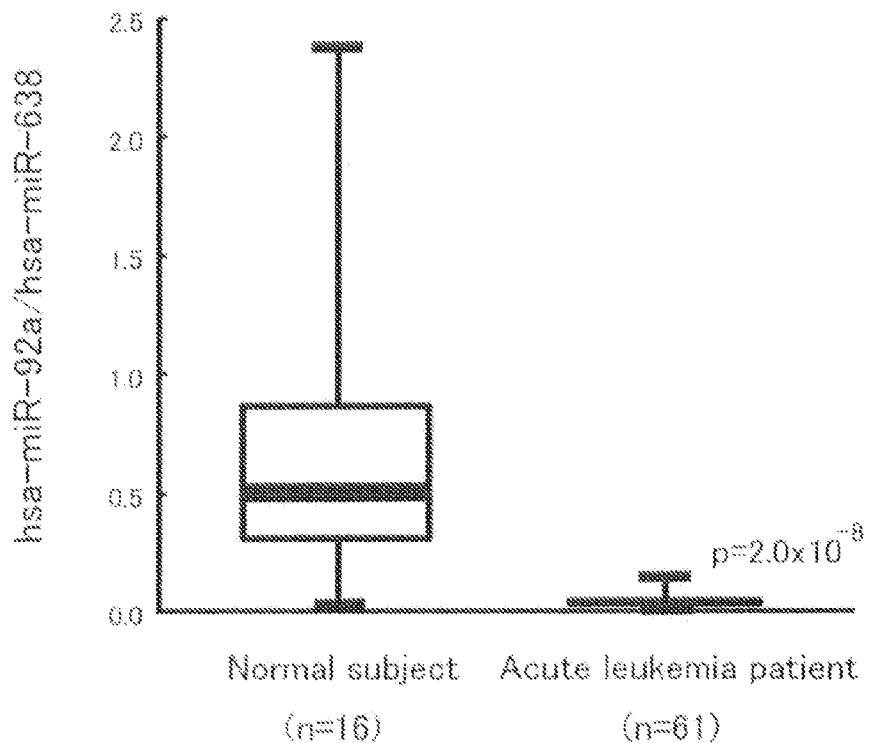
FIG. 3 is a graph showing the ratio (hsa-miR-92a/hsa-miR-638) between the fluorescence intensity of hsa-miR-92a as a cancer marker and the fluorescence intensity of hsa-miR-638 a correction marker in samples derived from normal subjects and in samples derived from acute leukemia patients in Example 3 of the present invention.

The result thereof is shown in FIG. 3. FIG. 3 is a graph showing the fluorescence intensity ratio (hsa-miR-92a/hsa-miR-638) with regard to the samples derived from the normal subjects and the samples derived from the acute leukemia patients. As can be seen from FIG. 3, with regard to the samples derived from the normal subjects, the fluorescence intensity ratios were as follows: median=0.4672; 25%=0.0051; 75%=0.0138; maximum value=2.3388; minimum value=0.0189; and average value=0.74587. On the other hand, with regard to the samples derived from the acute leukemia patients, the fluorescence intensity ratios were as follows: median=0.0129; 25%=0.0058; 75%=0.0274; maximum value=0.1085; minimum value=0.0004; and average value=0.020585. From this result, it was found that hsa-miR-92a expression decreased markedly in the samples derived from the patients. Furthermore, P value, which indicates the statistical significance of the difference between the normal subjects and the acute leukemia patients, was $2.0 \times 10^{-8}$, from which it was found that the difference was significant enough. The result described above demonstrates that hsa-miR-92a in serum or plasma is a particularly highly sensitive marker for acute leukemia.

Example 4

With regard to two pancreas cancer patients, hsa-miR-92a and hsa-miR-638 were measured in the same manner as in Example 3 before and after operation, and the fluorescence intensity ratio (hsa-miR-92a/hsa-miR-638) was calculated. As a result, relative values of the fluorescence intensity ratio after operation in the two patients assuming that the fluorescence intensity ratio before operation was 1 were 2.67 and 1.40, respectively. It can be seen from this result that the amount of hsa-miR-92a expressed decreases when a subject has pancreas cancer, and the amount of hsa-miR-92a expressed increases after the pancreas cancer is treated. That is, it can be said that it is possible to judge whether or not a subject has pancreas cancer based on the amount of hsa-miR-92a expressed.

Similarly, also with regard to four liver cancer patients, hsa-miR-92a and hsa-miR-638 were measured in the same manner as in Example 3 before and after operation, and the fluorescence intensity ratio (hsa-miR-92a/hsa-miR-638) was calculated. As a result, relative values of the fluorescence intensity ratio after operation in the four patients assuming that the fluorescence intensity ratio before operation was 1 were 6.13, 12.6, 156.52, and 12.12, respectively. It can be seen from this result that the amount of hsa-miR-92a expressed decreases when a subject has liver cancer, and the amount of hsa-miR-92a expressed increases after the liver cancer is treated. That is, it can be said that it is possible to judge whether or not a subject has liver cancer based on the amount of hsa-miR-92a expressed. It is to be noted that, with regard to other cancers, the similar results were obtained.

INDUSTRIAL APPLICABILITY

According to the present invention, by detecting the expression level of the cancer marker of the present invention in a biological sample, it becomes possible to judge the presence or absence of the development or progression of cancers with high reliability, for example. Furthermore, the cancer marker of the present invention provides a marked difference between negative and positive regarding the canceration, for example. Thus, according to the cancer marker of the present invention, it is possible to detect cancers at an initial stage whereas such detection is difficult by general palpation and the like

SEQUENCE LISTING

TF09011-0.5T25.txt

The invention claimed is:

1. An evaluation reagent for detecting a decrease in expression of hsa-miR-92 in a plasma or serum sample, wherein said evaluation reagent comprises an miRNA detection reagent capable of detecting hsa-miR-92, and wherein said evaluation reagent is capable of detecting a decrease in expression of hsa-miR-92 in a plasma or serum sample.

2. The evaluation reagent of claim 1, wherein the hsa-miR-92 is hsa-miR-92a.

3. The evaluation reagent of claim 1, wherein the miRNA detection reagent is a probe.

4. The evaluation reagent of claim 3, wherein the probe is labeled.

5. The evaluation reagent of claim 1, wherein the miRNA detection reagent is one or more primers.

6. The evaluation reagent of claim 5, wherein the miRNA detection reagent is one or more primers for real-time RT-PCR.

7. The evaluation reagent of claim 1, wherein the evaluation reagent further comprises one or more components selected from the group consisting of: an enzyme; a washing solution; a dissolving solution; a dispersing solution; and a diluent.

8. The evaluation reagent of claim 1, wherein the evaluation reagent is wet or dry.

9. An evaluation kit for detecting a decrease in expression of hsa-miR-92 in a plasma or serum sample, wherein said evaluation kit comprises an evaluation reagent comprising an miRNA detection reagent capable of detecting hsa-miR-92, and wherein said evaluation kit is capable of detecting a decrease in expression of hsa-miR-92 in a plasma or serum sample.

10. The evaluation kit of claim 9, wherein the hsa-miR-92 is hsa-miR-92a.

11. The evaluation kit of claim 9, wherein the miRNA detection reagent is a probe.

12. The evaluation kit of claim 11, wherein the probe is labeled.

13. The evaluation kit of claim 9, wherein the miRNA detection reagent is one or more primers.

14. The evaluation kit of claim 13, wherein the miRNA detection reagent is one or more primers for real-time RT-PCR.

15. The evaluation kit of claim 9, wherein the evaluation reagent further comprises one or more components selected from the group consisting of: an enzyme; a washing solution; a dissolving solution; a dispersing solution; and a diluent.

16. The evaluation kit of claim 9, wherein said evaluation kit further comprises a correction marker detection reagent.

17. The evaluation kit of claim 16, wherein said correction marker detection reagent is capable of detecting an hsa-miR-638.

18. The evaluation kit of claim 16, wherein the correction marker detection reagent is a probe.

19. The evaluation kit of claim 18, wherein the probe is labeled.

20. The evaluation kit of claim 16, wherein the correction marker detection reagent is one or more primers.

21. The evaluation kit of claim 20, wherein the correction marker detection reagent is one or more primers for real-time RT-PCR.

22. The evaluation kit of claim 16, wherein the correction marker detection reagent further comprises one or more components selected from the group consisting of: an enzyme; a washing solution; a dissolving solution; a dispersing solution; and a diluent.

* * * * *

UNITED STATES PATENT AND TRADEMARK OFFICE
CERTIFICATE OF CORRECTION

PATENT NO. : 9,169,520 B2  
APPLICATION NO. : 14/039835  
DATED : October 27, 2015  
INVENTOR(S) : Masahiko Kuroda et al.

It is certified that error appears in the above-identified patent and that said Letters Patent is hereby corrected as shown below:

IN THE SPECIFICATION

Column 17, Line 14: delete ""92a/638/B563")" and insert -- "92a/638/BS63") --

Column 17, Line 15: delete "[494/638/B563])" and insert -- [494/638/BS63]). --

Signed and Sealed this
Twenty-ninth Day of March, 2016

Michelle K. Lee
*Director of the United States Patent and Trademark Office*

SEQUENCE LISTING

<160> NUMBER OF SEQ ID NOS: 3

<210> SEQ ID NO 1
<211> LENGTH: 22
<212> TYPE: RNA
<213> ORGANISM: Homo sapiens

```
<400> SEQUENCE: 1
uauugcacuu gucccggccu gu                                      22

<210> SEQ ID NO 2
<211> LENGTH: 22
<212> TYPE: RNA
<213> ORGANISM: Homo sapiens

<400> SEQUENCE: 2
ugaaacauac acgggaaacc uc                                      22

<210> SEQ ID NO 3
<211> LENGTH: 25
<212> TYPE: RNA
<213> ORGANISM: Homo sapiens

<400> SEQUENCE: 3
agggaucgcg ggcggguggc ggccu                                   25
```